United States Patent [19]

Kwon et al.

[11] 4,348,537

[45] Sep. 7, 1982

[54] OLEFIN OXIDATION

[75] Inventors: Joon T. Kwon, Freehold Township, Monmouth County; Abraham P. Gelbein, Morristown, both of N.J.

[73] Assignee: The Lummus Company, Bloomfield, N.J.

[21] Appl. No.: 271,793

[22] Filed: Jun. 8, 1981

[51] Int. Cl.³ .............................................. C07C 67/055
[52] U.S. Cl. ................................. 560/243; 260/410.6; 560/1; 560/89; 560/112; 560/127; 560/198
[58] Field of Search ...................... 560/1, 89, 127, 198, 560/243, 244, 246; 260/410.6

[56] References Cited

U.S. PATENT DOCUMENTS

| | | | |
|---|---|---|---|
| 2,701,813 | 2/1955 | Snyder | 560/246 |
| 3,221,045 | 11/1965 | McKeon | 560/243 |
| 3,262,969 | 7/1966 | Clark | 560/243 |
| 3,637,818 | 1/1972 | Krekeler | 560/243 |
| 3,884,965 | 5/1975 | Kollar | 560/243 |
| 4,161,610 | 7/1979 | Klass | 560/243 |

FOREIGN PATENT DOCUMENTS

| | | | |
|---|---|---|---|
| 1176645 | 8/1964 | Fed. Rep. of Germany | 560/243 |
| 1191362 | 4/1965 | Fed. Rep. of Germany | 560/243 |
| 966809 | 8/1964 | United Kingdom | 560/243 |
| 1122444 | 8/1968 | United Kingdom | 560/243 |
| 1197843 | 7/1970 | United Kingdom | 560/243 |

*Primary Examiner*—Michael L. Shippen
*Attorney, Agent, or Firm*—Elliot M. Olstein; Louis E. Marn

[57] ABSTRACT

Olefin is oxidized in the absence of oxygen with a carboxylic acid in the presence of Mn(IV) oxide promoted with a noble metal to produce an effluent which includes mono and/or diester corresponding to the olefin and acid.

14 Claims, No Drawings

OLEFIN OXIDATION

This invention relates to the oxidation of olefins and more particularly to the production of esters, glycols and epoxy compounds from olefins. Still more particularly, the invention relates to the production of esters by reaction of an olefin with a carboxylic acid.

In accordance with the present invention, an olefin is oxidized by contacting the olefin with a carboxylic acid in the presence of Mn(IV) ion promoted with a noble metal to produce a reaction effluent which contains the corresponding mono and/or di ester corresponding to the olefin and carboxylic acid, and which may further include a corresponding glycol of the olefin and/or the corresponding epoxy derivative of the olefin.

Applicant has found that Mn(IV) ion is an active species for such oxidation and that such species when promoted with a noble metal is effective for oxidizing olefin with a carboxylic acid, as hereinabove described.

Applicant has further found that such oxidation may be accomplished in the absence of molecular oxygen, although oxygen could be present.

The Mn(IV) ion is provided as a Mn(IV) oxide; e.g., $MnO_2$; $MnO(OH)_2$; $MnO(CH_3COO)_2$; or may be generated in situ. Thus, for example, the Mn(IV) ion (as $MnO_2$ or derivative thereof) may be generated in situ as follows:

1. reaction of $AgMnO_4$ with $Mn(OOCCH_3)_2.4H_2O$ (Manganous acetate) in $CH_3COOH$
2. reaction $KMnO_4$ with $Mn(OOCCH_3)_2.4H_2O$ in $CH_3COOH$
3. oxidation of $Mn(OOCCH_3)_2$ in aq. NaOH with oxygen, air or mixtures thereof.
4. oxidation of $Mn(OOCCH_3)_2$ in aq. $NH_4OH$ with air, oxygen or mixtures thereof.

The selection of an optimum method for providing Mn(IV) ion is deemed to be within the scope of those skilled in the art from the teachings herein.

The noble metal may be either palladium, rhodium, iridium, osmium, ruthenium or platinum, with palladium being preferred. The noble metal employed as a promoter may be added as such, or may be generated in situ; for example, from a suitable salt. Thus, for example, palladium ($Pd°$) may be generated in situ from $Pd(NO_3)_2$. The Mn(IV) ion is employed in the reaction in an amount sufficient to effect the oxidation; as should be apparent the Mn(IV) ion should be present in amounts stoichiometrically sufficient to oxidize the desired amount of olefin. In the reaction, the Mn(IV) ion is converted to the Mn(II) species, and in accordance with the preferred embodiment, the Mn(IV) ion is employed in an amount whereby the product solution is nearly or wholly saturated with the Mn(II) species (about 2 mole/liter).

The noble metal is generally employed in an amount which provides from 0.001 to 0.20 atom (preferably from 0.005 to 0.05 atom) of noble metal per atom of Mn(IV). The selection of optimum amounts is deemed to be within the scope of those skilled in the art from the teachings herein.

The olefinically unsaturated hydrocarbon may have one or more olefinically unsaturated groups, including di- and polyolefins. The preferred compounds are mono-olefins. The mono-olefinically unsaturated hydrocarbon generally contains from 2–8 carbon atoms, preferably from 2–4 carbon atoms, with ethylene and propylene being preferred.

The carboxylic acid may be any acid which is stable to oxidation and which preferably forms esters with the olefin which are readily susceptible to hydrolysis. Thus, the carboxylic acid may be an aliphatic, aromatic or alicyclic acid and may contain one, two or more acid groups. The acid is preferably a hydrocarbon carboxylic acid, although the acid could include one or more substituent groups. The preferred acids are mono- and di- carboxylic acids which are either aliphatic or aromatic (having a single aromatic nucleus; e.g., benzoic acid). The alkanoic acids are most preferred, in particular those having 2–8 carbon atoms and in particular 2–4 carbon atoms, with acetic acid being most preferred. The acid may be employed, per se, or in an aqueous medium. Thus, for example, acetic acid may be employed as glacial or aqueous acetic acid. The acid functions as both a reactant and reaction medium, although it is possible to employ another liquid as the reaction medium.

The reaction is generally effected at temperatures of from 0° to 120° C., preferably at 20° to 40° C., and at pressures in the order of from 1 to 100 atm, preferably 1 to 5 atms. The selection of optimum temperatures and pressures is deemed to be within the scope of those skilled in the art from the teachings herein.

As hereinabove noted, the reaction may be accomplished in the absence of molecular oxygen, and the Mn(IV) ion is reduced during the process. It is possible to recover the reduced manganese and regenerate the manganese to the active form; i.e., Mn(IV) ion. Thus, for example, the reduced manganese compound may be dissolved or dispersed in an aqueous base and oxidized with oxygen (oxygen per se, air or oxygen enriched air) to the active Mn(IV) form.

The oxidation of olefin may be effected by dispersing the manganese compound [Mn(IV)] and noble metal (or salt convertible to the noble metal) in the acid followed by addition of the olefin; e.g., gaseous ethylene or propylene and reaction to produce the corresponding glycol mono- and/or di- ester. In most cases, the reaction product includes, in addition to the glycol mono- and/or diester, the corresponding epoxide and glycol of the olefin. It is to be understood, however, that other reaction systems are within the spirit and scope of the invention.

The following examples are included for the purposes of illustrating the invention, and it is to be understood that the scope of the invention is not to be limited thereby.

EXAMPLE 1

To a 50 ml-reactor provided with an agitator and a feed gas control device to maintain constant pressure, there is added 1.00 gm $AgMnO_4$ (4.40 mmole), 0.100 gm of $Pd(NO_3)_2$ (0.43 mmole) and 10.0 g 1/1 (wt/wt) aqueous acetic acid and the resulting mixture is agitated with a constant pressure of ethylene of about 5"-$H_2O$ above ambient pressure. After about 75 minutes, during which time the color of the slurry changed from pink to dark brown and then to light brown, it was determined that 4.76 mmole of ethylene is reacted. The reaction mixture is analyzed and primarily included ethylene glycol monoacetate with trace amounts of acetaldehyde, ethylene glycol and the diacetates (1,2- and 1,1-).

EXAMPLE 2

To the reaction vessel as described in Example 1, there is added 1.58 gms. KMnO$_4$ (10.0 mmole), 3.68 gms. Mn(OOCCH$_3$)$_2$.4H$_2$O (15.0 mmole) and 10.52 gms. 9/1 (wt/wt) aqueous acetic acid is admixed for a period of 5 minutes wherein a dark brown slurry was observed. The reaction vessel is then charged with ethylene as effected as aforesaid in Example 1 with no ethylene uptake observed after a period of 20 minutes. Thereafter 0.070 gms Pd(NO$_3$)$_2$ (0.30 mmoles) is added and there was ethylene uptake at an initial rate of 4 cc per minute which slowed down after about 10 minutes when the color of the slurry began to turn and its consistency became heavier. 10.0 gm of acetic acid is added to restore original consistency with ethylene being consumed at a steady rate of 0.8 cc per minute. After 2.5 hours, 152 cc (6.25 mmole) of ethylene was reacted.

Analysis of the mother liquor included acetaldehyde, ethylene glycol monoacetate, ethylidene glycol diacetate, and ethylene glycol diacetate, with selectivity to the ethylene glycol products being 19 mol %.

EXAMPLE 3

To a 0.51 capacity Parr hydrogenator assembly, there is added 0.135 gm Pd(NO$_3$)$_2$ (0.59 mmole), 7.35 gms Mn(OOCCH$_3$)$_2$.4H$_2$O, 3.16 gm KMnO$_4$ in 60.09 gm glacial acetic acid. The mixture is agitated for a period of 10 minutes to yield 50.0 mmole of MnO(OOCCH$_3$)$_2$. The vessel is then charged with 30.0 psig ethylene with a total of 46 mmoles of ethylene being introduced in 6 hours. The resulting slurry is separated by centrifugation to provide 9.98 gms of a brownish-white precipitate, 29.45 gms of a mother liquor and 7.46 gms of wash liquors. The liquors are analyzed to find acetaldehyde, ethylene glycol, ethylene glycol monoacetate, ethylidene glycol diacetate and ethylene glycol diacetate with selectivity to the ethylene glycol products being 80.4%.

EXAMPLE 4

The procedure of Example 3 is repeated in 9/1 aqueous acetic acid with a total of 40.9 mmole of ethylene added in 7 hours. Separation of the product mixture resulted in 10.31 gms of a reddish brown residue, 0.10 gms of a black powder (palladium black mainly, calculated content 0.063 gms), 44.44 gms of a nearly colorless mother liquor and 30.37 gms of a yellow wash liquor.

Such liquors are analyzed and contained actaldehyde, ethylene glycol, its monoacetate and diacetate, and ethylidene glycol diacetate with a selectivity to the ethylene glycol products of 50.9%.

EXAMPLE 5

The procedure of Example 3 is repeated with propylene in glacial acetic acid at a pressure of 25 psig. After 7 hours, 44.9 mmole propylene is added resulting in a reddish-brown slurry yielding 28.04 gms of a yellow wash liquor with a total of 12.50 gms precipitate. The liquors contain propionaldehyde, the monoacetate and the diacetate of 1,2-propanediol and trace quantities of 1,2- and 1,3-propanediol with a selectivity to the 1,2-diol products of 92 mol %.

EXAMPLE 6

The procedure of Example 5 is repeated with 9/1 aqueous acetic acid with 26.3 mmole propylene.

The resulting slurry after dilution with 15.69 gms of acid resulted in 29.85 gms pale-yellow mother liquor, 33.85 gms yellow wash liquors with 10.05 gms precipitate. Analysis of the liquors gave propionaldehyde, 1,2-propanediol, its monoacetate and diacetate. The Example have a selectivity to the 1,2-diol products of 65 mole %.

EXAMPLE 7

To the apparatus there is added 49.02 gms of Mn(OOCCH$_3$)$_2$.4H$_2$O (0.20 mole) and 240 ml of 2.0 N aq. NaOH. The apparatus is pressurized with oxygen to 25.0 psig and shaken for 24 hours for a 94.5 mmole uptake (theoretical-100 mmole) of oxygen.

One-half of the resulting water-washed wet cake (calculated Mn content 100.0 mmole) is slurried in 110 gms glacial acetic acid with 0.160 g Pd(NO$_3$)$_2$ (0.70 mmole), and subsequently pressurized with propylene to provide a total uptake of 72.1 mmole in 6 hours. The resulting product is separated into 75.26 gms yellow mother liquor, 45.11 gms brown wash liquors and 15.05 gms of a precipitate. The liquor contains the following products: propionaldehyde, 1,3-propanediol, 1,2-propanediol, and mono and di-acetates thereof. The Example illustrates a selectivity of 60.6 mole % to the 1,2-diol products.

EXAMPLE 8

The remaining one-half portion of the water-washed wet cake of Example 7 is slurried in 80.0 gms 1/1 mixture of acetic anhydride and glacial acetic acid together with 0.70 mmole Pd(NO$_3$)$_2$. After pressurization of propylene for a period of 6 hours, there is effected a 68.8 mmoles uptake of propylene.

The resulting product is separated into a liquor and precipitate with the products in the liquor being propylaldehyde, 1,3-propanediol, 1,2-propanediol and its monoacetate and its diacetate. This Example illustrated a selectivity of 74.8 mole % to the 1,2-diol product.

EXAMPLE 9

13 g. of the precipitate of Example 7 (50 mmole Mn(II) calculated is introduced into the apparatus with 63.51 gms concentrated NH$_4$OH and mixed under air pressure of 30.0 psig and subsequently an atmosphere of oxygen at a pressure of 30.0 psig for a period of 3 hours. The resulting cake after water-washing is slurried with 60.09 gms of glacial acetic acid together with 0.210 gms of palladium black recovered from previous runs to provide a palladium content of 0.04 mole/mole Mn. The resulting mixture is combined with 30.0 psig ethylene and reacted for 7 hours (ethylene uptake - 25.6 mmole) resulting in a liquor containing acetaldehyde, ethylene glycol monoacetate, ethylene glycol diacetate and traces of glycol and ethylidene diacetate with a selectivity to ethylene glycol of 81.5 mole %.

Such example illustrates the ability to regenerate the oxidant.

EXAMPLE 10

In the Parr apparatus, 12.25 gms Mn(OOCCH$_3$)$_2$.4H$_2$O (50 mmole) and 69.92 grm conc. NH$_4$OH were shaken together for 20 minutes. The vessel was then charged with 30.0 psig air and the oxidation carried out as before. A total of 11.4 psig oxygen make-up was needed in 3 hours for an oxygen uptake of 15.8 mmole where the calculated uptake was 25.0 mmole (63.2%). The water-washed wet cake was washed with acetone and vacuum-dried to give 4.04 grm of a charcoal-black powder. The theoretical yield as MnO(OH)$_2$ was 5.25 grm (77.0% yield). The product assay was 98.4%.

A portion of this powder (3.20 grm, 30.0 mmole) was dispersed in 50.00 grm of 9/1 aq. acetic acid in the Parr apparatus with 0.100 grm of palladium black recovered from previous runs and the vessel charged with ethylene at 30.0 psig. A total of 19.9 mmoles ethylene was taken up in 6 hours.

Separation of the product mixture gave 24.97 grm of yellow mother liquor, 7.895 grm of brown precipitate, 9.78 grm wash liquor and 0.10 grm of a black precipitate. The liquors contained acetaldehyde, ethylene glycol monoacetate, ethylene glycol diacetate and trace quantities of ethylene glycol, vinyl acetate and ethylidene glycol diacetate.

Selectivity to ethylene glycol products was 82.7 mole %.

The present invention is particularly advantageous in that it is possible to accomplish the oxidation at or near ambient temperature and by the use of inexpensive manganese. Moreover, the active form of the manganese may be regenerated by simple reoxidation and separation steps. These and other advantages should be apparent to those skilled in the art from the teachings herein.

Numerous modifications and variations of the above disclosed invention are possible in light of the above teachings and, therefore within the scope of the appended claims the invention may be practised otherwise than as particularly described.

What is claimed is:

1. In a process for preparing glycol mono- and diesters comprising oxidizing an olefin in the presence of a carboxylic acid and water, the improvement comprising:
    contacting the olefin, water and the carboxylic acid in the presence of Mn(IV) ion and a noble metal.

2. The process of claim 1 wherein the Mn(IV) ion is present as an Mn(IV) oxide.

3. The process of claim 2 wherein the olefin is a mono-olefinically unsaturated hydrocarbon and the acid is an alkanoic acid.

4. The process of claim 3 wherein the olefin has from 2-8 carbon atoms.

5. The process of claim 4 wherein the alkanoic acid has from 2-6 carbon atoms.

6. The process of claim 5 wherein the alkanoic acid is present as an aqueous solution thereof.

7. The process of claim 5 wherein the noble metal is palladium.

8. The process of claim 7 wherein the noble metal is generated in situ from a salt thereof.

9. The process of claim 7 wherein the acid is acetic acid.

10. The process of claim 9 wherein the contacting is effected in the absence of molecular oxygen.

11. The process of claim 10 wherein the olefin is propylene.

12. The process of claim 10 wherein the olefin is ethylene.

13. The process of claim 3 wherein the reaction is effected in the absence of molecular oxygen.

14. The process of claim 3 wherein the Mn(IV) oxide is reduced in the oxidation and the reduced manganese compound is oxidized to regenerate Mn(IV) oxide for reuse in the process.

* * * * *